United States Patent [19]

Morrison

[11] Patent Number: 4,614,870

[45] Date of Patent: Sep. 30, 1986

[54] MINIATURE ISOTOPIC SOIL MOISTURE GAGE

[75] Inventor: Roderick G. Morrison, Carlsbad, Calif.

[73] Assignee: Sunburst Energy Systems, Inc., San Marcos, Calif.

[21] Appl. No.: 558,378

[22] Filed: Dec. 5, 1983

[51] Int. Cl.$^4$ ............................................. G01N 23/08
[52] U.S. Cl. .............................. 250/358.1; 250/252.1; 250/253; 378/53
[58] Field of Search ...................... 250/390, 253, 358.1, 250/370, 252.1; 378/53

[56] References Cited

U.S. PATENT DOCUMENTS

| | | | |
|---|---|---|---|
| 3,602,713 | 8/1971 | Kastner et al. | 250/390 |
| 3,843,887 | 10/1974 | Morrison | 250/358.1 |
| 3,879,607 | 4/1975 | Bjorklund | 250/252.1 |
| 3,975,641 | 8/1976 | Morrison | 378/52 |

OTHER PUBLICATIONS

Fishman, "Gamma Transmission Gauge for Assay of Integral Water Content in Soil", Nucl. Instr. & Methods, 184, (2,3), Jun. 1, 1981, pp. 571–576.

Primary Examiner—Carolyn E. Fields
Attorney, Agent, or Firm—Baker, Maxham & Jester

[57] ABSTRACT

A miniature, low power consuming, density gage utilizing extremely small artificial and naturally found radioactive sources. The gage employs a unique method of compensating for the gamma attenuation coefficient in different materials such as soils to provide a very simple but accurate and effective moisture gage. A single source emits radiation beams, one through a control sample of the material and at least one beam through a zone of the material where moisture content is to be determined. The apparatus may optionally be employed to control a crop irrigation system to maintain moisture within the comfort zone of the plants growing in the soil. The invention also may be used for measuring moisture content in several discrete zones of the material.

7 Claims, 6 Drawing Figures

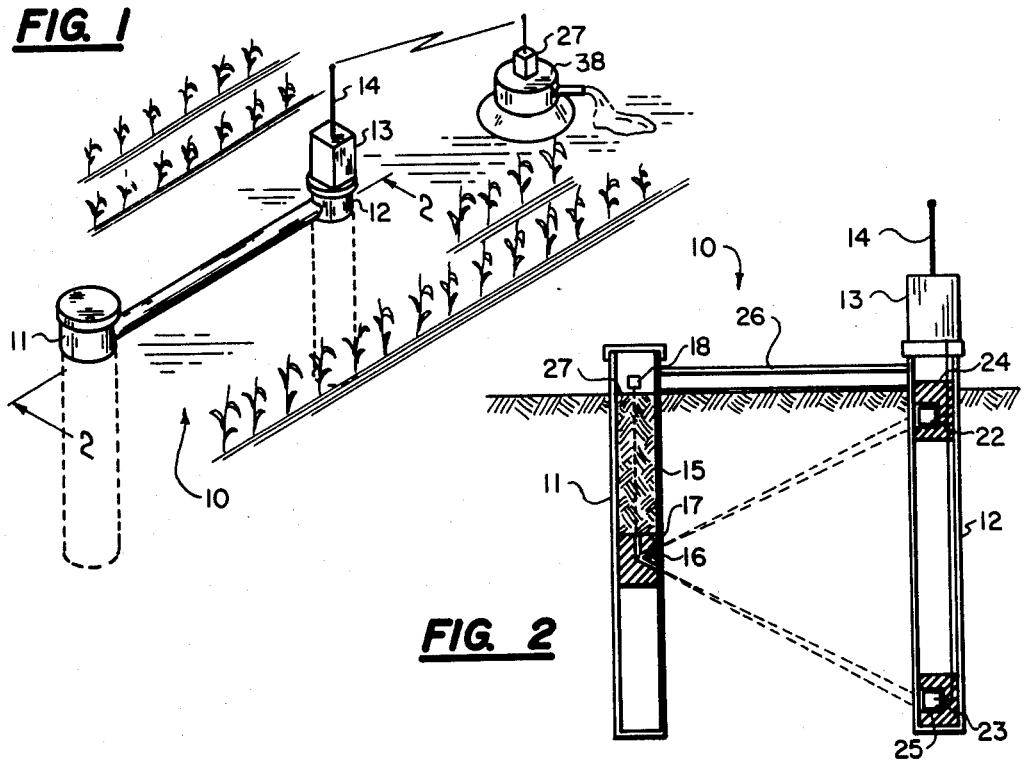
FIG. 1
FIG. 2
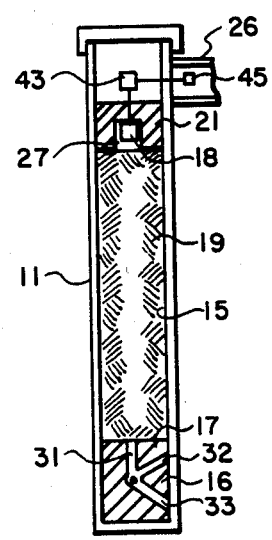
FIG. 3
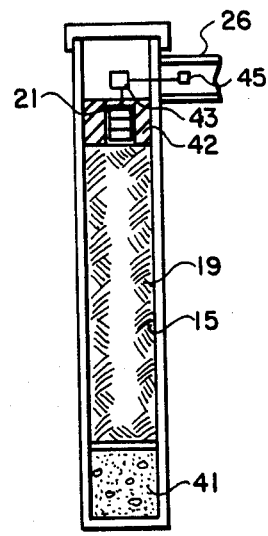
FIG. 4

MINIATURE ISOTOPIC SOIL MOISTURE GAGE

This invention relates to the accurate monitoring of soil moisture content in a variety of applications where minimum perturbation of the measurement zone is required, where it is desirable to utilize the smallest isotopic source practicable, and where environment and soil conditions vary over a wide range.

The present invention is related to my prior patents, U.S. Pat. No. 3,843,887 and U.S. Pat. No. 3,975,641. This invention utilizes some techniques disclosed in the prior patents but provides a significant advance in broader application to the needs described herein.

The present techniques utilizing radioactive isotopes for measurement of precipitation in the form of snow water content and soil moisture content are described in the above mentioned patents. The shortcomings of these devices are hereafter described along with the improvements claimed with this invention.

U.S. Pat. No. 3,843,887 disclosed a method of measuring the desired parameter in fixed zones which were stacked according to the needs of the particular area of use. Since the use of high energy gamma emitters was desirable, a self-calibrating source decay scheme was used to avoid any error in half life correction for short lived isotopes such as Cobalt-60. These devices are now operating into the third half life of the decay experienced with Cobalt-60. That instrument has come to be known as the "Zig Zag Isotopic Gage".

With regard to U.S. Pat. No. 3,975,641 a precipitation gage was introduced which utilized naturally found radioactive materials held together with suitable binders and arranged in a preferred geometry which produced maximum counting efficiency for a given radiation detector. This gage has come to be known as the "Hot Rocks Gage".

Nuclear soil moisture gages are in use which use both the attenuation and backscatter principle. A neutron backscatter gage in use typically has a neutron source comprised of a selective group of transuranic elements such as plutonium, polonium, or californium coupled with backscattering material such as beryllium. The source is shielded from the detector with some form of neutron absorbing material such as boron. Because of the high energy of the neutrons, considerable distance is required between the source and the detector which limits the resolution of the desired water content measurement. In addition, these devices use sizeable neutron sources which require careful handling by the user, and licensing by federal or state agencies. The sources used emit highly energetic neutrons which have an average energy of greater than 1 Mev. When the neutrons interact with hydrogenous material, they scatter at energies of less than their starting energy. The hydrogen in water tends to thermalize a high percentage of these neutrons, and a measure of the number of thermalized neutrons provides a good index of the amount of water present. In many soils there are significant amounts of lithium. Lithium is also a good material for thermalization of neutrons and can produce an inaccurate reading with respect to absolute water present. In short, the neutron backscatter gage has three shortcomings apparent; size of neutron source from a biological safety standpoint which requires careful handling and licensing, relatively poor resolution because of its size, and it is subject to errors created by soil elements which may be present.

Gamma backscatter and attenuation gages are both in use as soil moisture detectors. These gages require relative large sources and require state or federal licensing. The attenuation gages use essentially the same principle as described in my aforementioned patents. To get high accuracy they sometimes use larger detectors such as ion chambers or scintillators coupled to photomultiplier detectors. In these applications a higher voltage than is required by Geiger-Mueller (GM) tubes is required. For good resolution, the detector must be as small as possible. For hostile environments where high humidity is prevalent, high voltage breakdown occurs frequently and the field performance of these devices has been shown to be short in duration. In addition, the size and high voltage require extensive power supplies which limit field use to relatively short periods of time. The gamma backscatter gages in use suffer from the same drawbacks as outlined for the attenuation gages. Another serious deficiency common to both of the gamma gages is related to the parameter being measured. Specifically counting efficiency is related to the total attenuation which follows the natural log of the number of counts, which is proportional to the density of the substance. That relationship is expressed as $\ln_e {-\mu\rho\tau}$ where $\mu$ is the gamma mass attenuation coefficient and is related to the source energy, $\rho$ is the absolute density of the material being measured, and $\tau$ the distance between the source and detector. Soils vary widely in composition, some with high density materials such as iron and some with a large amount of silicon dioxide. At 1 Mev, iron has a mass attenuation coefficient of 0.0599, SiO has 0.0636, and water has 0.0707. The combination of the u term can give erroneous results if some form of correction is not used. It is the density factor $\rho$ that is directly proportional to moisture content in a substance.

Other non-nuclear methods are in use which are used to determine soil moisture content. The most commonly used instrument is called a tensiometer. This device is, in effect, a sensitive pressure gage which is activated by changes in pressure created in a hygroscopic membrane in contact with the soil. As the soil dries out, changes in pressure are related to the percent of moisture present. These devices are fragile and subject to membrane fouling, especially brought about by materials soluble in water, such as chemical fertilizers and salts found in most irrigation water. In addition, rapid changes in soil moisture can break the vacuum in the pressure column thus taking the indicator full scale. Another device in use is commonly called a "Salt Block". In this technique, a block of material such as gypsum is instrumented with two conductive leads and buried in the soil of interest. By applying a voltage to the leads and measuring the current between electrodes, an index of moisture is obtained from the change in resistance brought about by the hygroscopic moisture absorbed by the gypsum. These devices are more susceptible than the tensiometer to fouling by conductive impurities in the water and have an inordinate time lag in recovery to rapid changes in soil moisture content. A third device in use is comprised of a salted metal, typically iron, impregnated with an etch of acid, an insulator and a conductor such as stainless steel. A sensitive meter completes the circuit which is activated by the contact potential generated when the salted metal comes in contact with moisture. Current returns through the stainless steel and activates the meter. These devices, while relatively cheap and requiring no external voltage, are fragile and susceptible to the aforementioned fouling. In the critical plant comfort zone (55% to 95% field capacity), this device has very poor accuracy. A fourth device not in common use because of its large size is called a capacitance gage. This device is comprised of two parallel plates which use the soil as a dielectric. By measurement of changes in capacitance, a correlation to water content can be inferred. The accuracy from small plates is very marginal, and the resolution of large plates makes them an unattractive tool.

It is, therefore, the principle object of this invention to provide a soil moisture gage which reduces the size of the device, reduces the source assay to eliminate any biological hazard to the user, reduces the voltage and power requirement to enable long and unattended use, and to compensate for the gamma attenuation factor for differing soil compositions. It is further the object of this invention to provide a radioactive source of gamma emitting energies of sufficient strength to penetrate reasonable distances through saturated soil, said source to be either artifically produced or found in nature and of low enough assay to be exempt from licensing or qualified for General Licensing thus relieving the user of regulatory constraints in use.

BRIEF DESCRIPTION OF THE DRAWING

These, together with other objects and advantages which will become subsequently apparent, reside in the details of construction and operation as fully hereinafter described and explained, reference being had to the accompanying drawings forming a part hereof wherein like numerals refer to like parts throughout.

FIG. 1 is a perspective view of a typical installation of the invention.

FIG. 2 is a cross sectional view taken substantially through cutting plane 2—2 of FIG. 1.

FIG. 3 is an enlarged sectional view of the source and reference chamber showing greater detail of the method of compensating for varying gamma attenuation coefficients.

FIG. 4 is a sectional view similar to FIG. 3 showing a source of naturally found radioactivity of sufficient assay to be used in the invention

DESCRIPTION OF THE PREFERRED EMBODIMENTS

Figure 5:
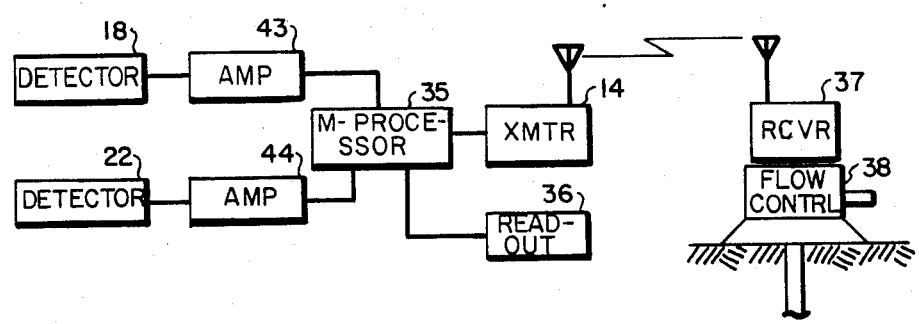
FIG. 5 is a black diagram of the device indicating the basis for small size and lower power consumption.

Referring now to the drawings in detail, the embodiment illustrated in FIGS. 1 and 2, the gage system generally denoted as reference 10 and is constituted of a suitable moisture proof housing 11, detector tube 12, electronic signal acquisition and manipulation microprocessor 13 and radio transmitter 14. The moisture proof housing comprises a soil reference chamber 15, radioactive source 16 embedded in lead source collimator 17 and miniature solid state reference detector 18. The detector tube houses miniature solid state measurement detectors 22 and 23 detector lead collimators 24 and 25. The housing and detector tube are coupled together and spaced by a predetermined distance by spacer bar 26.

Radioactive source 16 is positioned a predetermined distance below the soil surface with detector 22 approximately at the surface and detector 23 at a depth approximately twice the depth of the source. This establishes two measurement zones, one from surface detector 22 to the depth of the source and the other from the depth of the source to the depth of detector 23. The soil moisture measurement for each zone represents the integrated moisture of the zone rather than a point moisture measurement.

The first major improvement disclosed herein is the small size available in the solid state detectors 18, 22, and 23. Cadmium telluride has been developed as a nuclear counter and is now cost competitive with the GM tubes. A crystal detector of 5 mm × 5 mm × 2 mm in size is up to 1,000 times more efficient on a volumetric basis than gas tubes such as GM tubes or ion chambers. In addition to the small size, very small unregulated power supplies are used, typical 10 to 20 volts DC to bias the semiconductor (said power supply can be ordinary transistor batteries). The second major improvement disclosed is in the reference chamber 15, which enables the apparatus to be self calibrated a sample soil 19 is removed from the ground under study, weighed, dried, reweighed and inserted into the reference chamber. A moisture tight cap 27 is placed over the tube containing the dry soil. This soil column then serves as a reference zone of material typical of the existing field soil and will have the exact gamma attenuation coefficient ($\mu$) and density ($\rho$) as the soil being measured, with the only difference being the amount of moisture removed at the onset of the measurement. The difference in weight of the removed soil serves as the starting moisture content and is logged on the attenuation curve furnished with the instrument. If the instrument is moved from one location to another, the reference tube is cleared of the previous soil with the new soil sample conditioned as described, or the old reference tube may be retained for subsequent use in the original starting point.

Referring now to FIGS. 2, 3 and 5, the signals received by reference detector 18 are programmed for a specific number of counts in computation means such as microprocessor 35 (e.g., 20,000) at which time the counts started concurrently in measurement detector 24 are terminated. Thus the microprocessor has a comparator function to match detected counts with a predetermined number of counts. Measurement detector 23 functions in the same way and will not now be discussed in detail. The ratio of the dry soil count to the measured soil count is then computed by microprocessor 35 and transmitted to an appropriate output device such as readout device 36 or transmitter 14, or both. For remote irrigation control, a signal representing moisture content can be transmitted to receiver 37 for control of device 38 such as a pump, sprinkler or head gate. The microprocessor can further be programmed to initiate a command to turn water on when the soil moisture reaches 55% of field capacity and turn it off when it reaches 90% of field capacity. This range is considered optimum for plant growth. Field capacity is defined as the maximum amount of water a given soil can hold against gravity. The third improvement disclosed herein has to do with the small size of the device. Housing 11 and tube 12, can be as small as 1.5 cm in diameter. This enables the user to make extremely small holes in the field. The microprocessor, transmitter and receiver can be housed in a container 5 cm × 10 cm × 2 cm, and the power supply requirement can be reduced to less than 1/100 that of existing gages.

Figure 6:
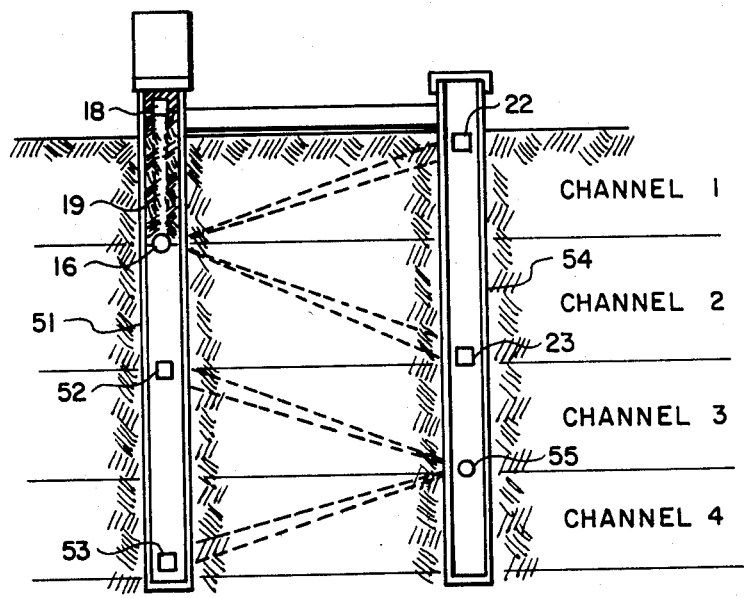
FIG. 6 is a sectional view similar to FIG. 2 showing a multiple zone moisture detecting installation.

Referring now to FIG. 4, source 41 made of a naturally occuring source of radiation, as described in U.S. Pat. No. 3,975,641 has been found to have sufficient penetrating power of emitted gamma rays to serve as a natural radioactive source through up to 25 cm of saturated soil. A source of a diameter of 2 cm and a length of 5 cm can produce sufficient radiation counts to obtain the desired readings. The disadvantage being that this size of natural source may take ten times as long to generate sufficient counts to obtain the number of counts equivalent to those generated by a 1 mCi artifical source of Co-60. Referring again to FIG. 4, the parts are the same as the parts depicted in FIG. 3 except that detector 42 may be stacked (i.e., multiple detectors 5 mm×5 mm×2 mm one on top of the other with insulation between) to increase sensitivity and shorten the counting time. Natural radioactive source 41 may be up to 2 cm in diameter thus requiring a large diameter for the access hole. It should be recognized that the natural radiation source can be made at lower cost (i.e., an order of magnitude less than the artificial source) thus giving the user the option of permanently placing many sources under the soil surface with no safety requirement or licensing problem. It is possible that either the artificial or natural sources can be stacked at discrete soil depths accompanied with companion detectors to provide as many measurement zones of interest as are needed (similar to the gage shown in U.S. Pat. No. 3,843,887) and shown generally in FIG. 6. In housing 51, equivalent to housing 11 in FIG. 3, there is not only soil sample 19, source 16 and detector 18, but measurement detectors 52 and 53. In tube 54, equivalent to tube 12 in FIG. 2, is second source 55, in addition to detectors 22 and 23. These are indicated in FIG. 6 as channels 1, 2, 3 and 4 which are the material measurement channels or zones.

Referring more specially to FIG. 5, the measurement is obtained electronically by photon interaction with reference detector 18. The signal from that detector is amplified immediately next to the reference detector by means of a field effect transistor and discrete amplifier 43 and fed to the microprocessor 25. The signals from measurement detector 22 are conditioned in a like manner by amplifier 44. When the system is turned on, both circuits begin counting and the respective counts are stored in the microprocessor. When the reference detector counts reach a pre-selected value, the microprocessor terminates the counting in the measurement detector.

Amplifier 43 is shown in FIGS. 3 and 4 together with connector 45. The wires from the microprocessor are coupled by means of this connector. The microprocessor then operates arithmetically on the count numbers to provide a specific soil moisture content which may then be displayed on readout 36. For automatic moisture control microprocessor 35 is programmed to shut off or turn on the water source 38 by means of radio transmitter 14 and receiver 37. The ON-OFF program is defined by the user to cover the desired range of moisture according to the particular soil field capacity.

The foregoing is considered illustrative only of the principles of the invention. Further since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A gage for monitoring the moisture content in a material, said gage comprising:

means for compensating for any variables in radiation attenuation coefficient in the material being monitored, said means comprising a reference column of the material in a calibrated state of moisture content;

a source of radiation of sufficiently small size so as to possess no known substantial biological hazards, said source being positioned at one end of said reference column of material;

reference detector means spaced from said radiation source by the length of said reference column of material and producing a series of output pulses proportional in number to the detected radiation intensity from said source through the reference column of material;

measurement detector means spaced a predetermined distance from said source, substantially all of the space between said source and said measurement detector means being occupied by the material being monitored, said measurement detector means producing a series of output pulses proportional to the detected radiation intensity from said source through the material being monitored;

computation means connected to both said detector means for counting the output pulses from said reference detector means and said measurement detector means, said counting means including comparator means and means for stopping the measurement detector means count when the reference detector means count reaches a predetermined value;

means for converting the count difference between said reference and measurement detector means outputs to a signal representing moisture content of the material being monitored; and means for providing an output signal representing the moisture content of the monitored material, said output signal being adapted to be coupled to indicator means.

2. The gage recited in claim 1, wherein:

said means for compensating comprising said reference column which is replaceable with like reference columns of different materials to be monitored said means for compensating allowing selective monitoring of the moisture content of those different materials.

3. The gage recited in claim 1, wherein said measurement detector means comprises two spaced detectors substantially equal distances from said source, each of said spaced detectors measuring the output of said source through different zones of interest of the material being monitored.

4. The gage recited in claim 1, and further comprising:

a plurality of spaced sources of radiation of sufficiently small size so as to possess no substantial biological hazards;

said measurement detector means comprising a plurality of measurement detectors arranged in multiple zones of interest with respect to said radiation sources to enable the determination of moisture content of a plurality of selected zones at different depths in said material.

5. The gage recited in claim 1, wherein said source of radiation is a source of natural radioactivity requiring no license for use by regulatory agencies.

6. The gage recited in claim 1, and further comprising:

a transmitter coupled to said output signal providing means;

a receiver means adapted to receive signals from said transmitter and produce output signals corresponding thereto; and flow control means for controlling the amount of moisture added to the material being monitored, said flow control means being controlled by the signals from said receiver means.

7. The gage recited in claim 1, wherein the calibrated state of the reference column of material is bone dry.

* * * * *